United States Patent
Chen (10) Patent No.: US 7,101,403 B2
(45) Date of Patent: Sep. 5, 2006

(54) VIBRATION-ABSORBING DEVICE FOR AN ARTIFICIAL LOWER LIMB

(76) Inventor: Sen-Jung Chen, No. 236, Sec. 3, Ho-Ping W. Rd., Taipei (TW)

( * ) Notice: Subject to any disclaimer, the term of this patent is extended or adjusted under 35 U.S.C. 154(b) by 329 days.

(21) Appl. No.: 10/856,910

(22) Filed: May 28, 2004

(65) Prior Publication Data

US 2005/0267601 A1    Dec. 1, 2005

(51) Int. Cl.
*A61F 2/80* (2006.01)
*A61F 2/66* (2006.01)

(52) U.S. Cl. .............................. 623/35; 623/27; 623/50

(58) Field of Classification Search ................... 623/27, 623/35, 38, 46–52
See application file for complete search history.

(56) References Cited

U.S. PATENT DOCUMENTS

| | | | | |
|---|---|---|---|---|
| 3,706,465 A | * | 12/1972 | Olowinski | 74/99 R |
| 4,883,493 A | * | 11/1989 | Martel et al. | 623/38 |
| 5,984,972 A | * | 11/1999 | Huston et al. | 623/35 |
| 6,080,197 A | * | 6/2000 | Chen | 623/27 |
| 6,214,056 B1 | * | 4/2001 | Wilkinson | 623/35 |
| 6,302,918 B1 | * | 10/2001 | Gramnas | 623/27 |
| 6,488,717 B1 | * | 12/2002 | McColl et al. | 623/35 |
| 2003/0018393 A1 | * | 1/2003 | Skiera | 623/35 |

* cited by examiner

*Primary Examiner*—Bruce Snow
(74) *Attorney, Agent, or Firm*—Frommer Lawrence & Haug LLP; Ronald R. Santucci (57) ABSTRACT

A vibration-absorbing device for an artificial lower limb includes a knee-connecting tube attached to a prosthetic knee unit, an ankle-connecting member attached to a prosthetic foot and ankle unit, and an upright connecting rod having an upper end disposed movably within the tube, and a lower end connected fixedly to the ankle-connecting member. A coiled compression spring is sleeved on the connecting rod between the knee unit and the foot and ankle unit so as to bias the connecting rod to move downwardly relative to the tube to a predetermined position, thereby retarding movement of the connecting rod in an axial direction of the tube. A cushion member is made of a resilient material, is sleeved on the ankle-connecting member, and is disposed within the tube so as to retard movement of the connecting rod in a transverse direction of the tube.

4 Claims, 7 Drawing Sheets

VIBRATION-ABSORBING DEVICE FOR AN ARTIFICIAL LOWER LIMB

BACKGROUND OF THE INVENTION

1. Field of the Invention

This invention relates to a vibration-absorbing device for an artificial lower limb, and more particularly to a vibration-absorbing device that is disposed between a prosthetic knee unit and a prosthetic foot and ankle unit and that includes a longitudinal damping unit and a transverse damping unit.

2. Description of the Related Art

Figure 1:
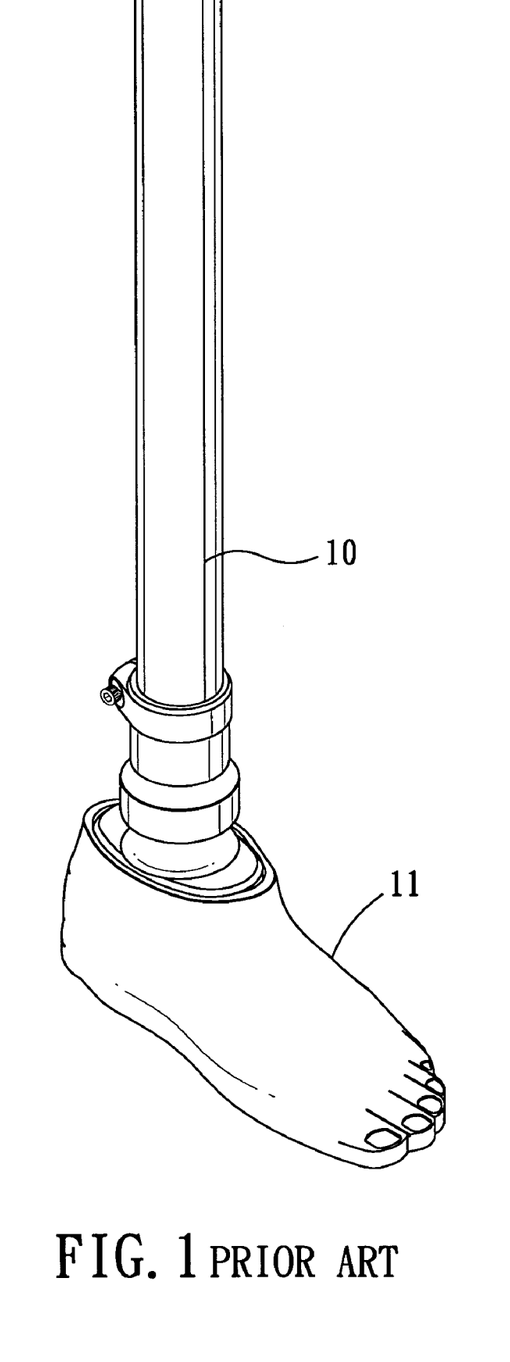
FIG. 1 is a perspective view of a conventional artificial lower limb.

Referring to FIG. 1, a conventional artificial lower limb is shown to include a foot rod 10 and a prosthetic foot and ankle unit 11. No vibration-absorbing device is disposed on the lower limb, thereby giving discomfort to a prosthesis wearer while walking.

SUMMARY OF THE INVENTION

The object of this invention is to provide a vibration-absorbing device for an artificial lower limb.

According to this invention, a vibration-absorbing device for an artificial lower limb includes a knee-connecting tube attached to a prosthetic knee unit, an ankle-connecting member attached to a prosthetic foot and ankle unit, and an upright connecting rod having an upper end disposed movably within the tube, and a lower end connected fixedly to the ankle-connecting member. A coiled compression spring is sleeved on the connecting rod between the knee unit and the foot and ankle unit so as to bias the connecting rod to move downwardly relative to the tube to a predetermined position, thereby retarding movement of the connecting rod in an axial direction of the tube. A cushion member is made of a resilient material, is sleeved on the ankle-connecting member, and is disposed within the tube so as to retard movement of the connecting rod in a transverse direction of the tube.

BRIEF DESCRIPTION OF THE DRAWINGS

These and other features and advantages of this invention will become apparent in the following detailed description of the preferred embodiments of this invention, with reference to the accompanying drawings, in which.

DETAILED DESCRIPTION OF THE PREFERRED EMBODIMENTS

Before the present invention is described in greater detail in connection with the preferred embodiments, it should be noted that similar elements and structures are designated by like reference numerals throughout the entire disclosure.

Figure 2:
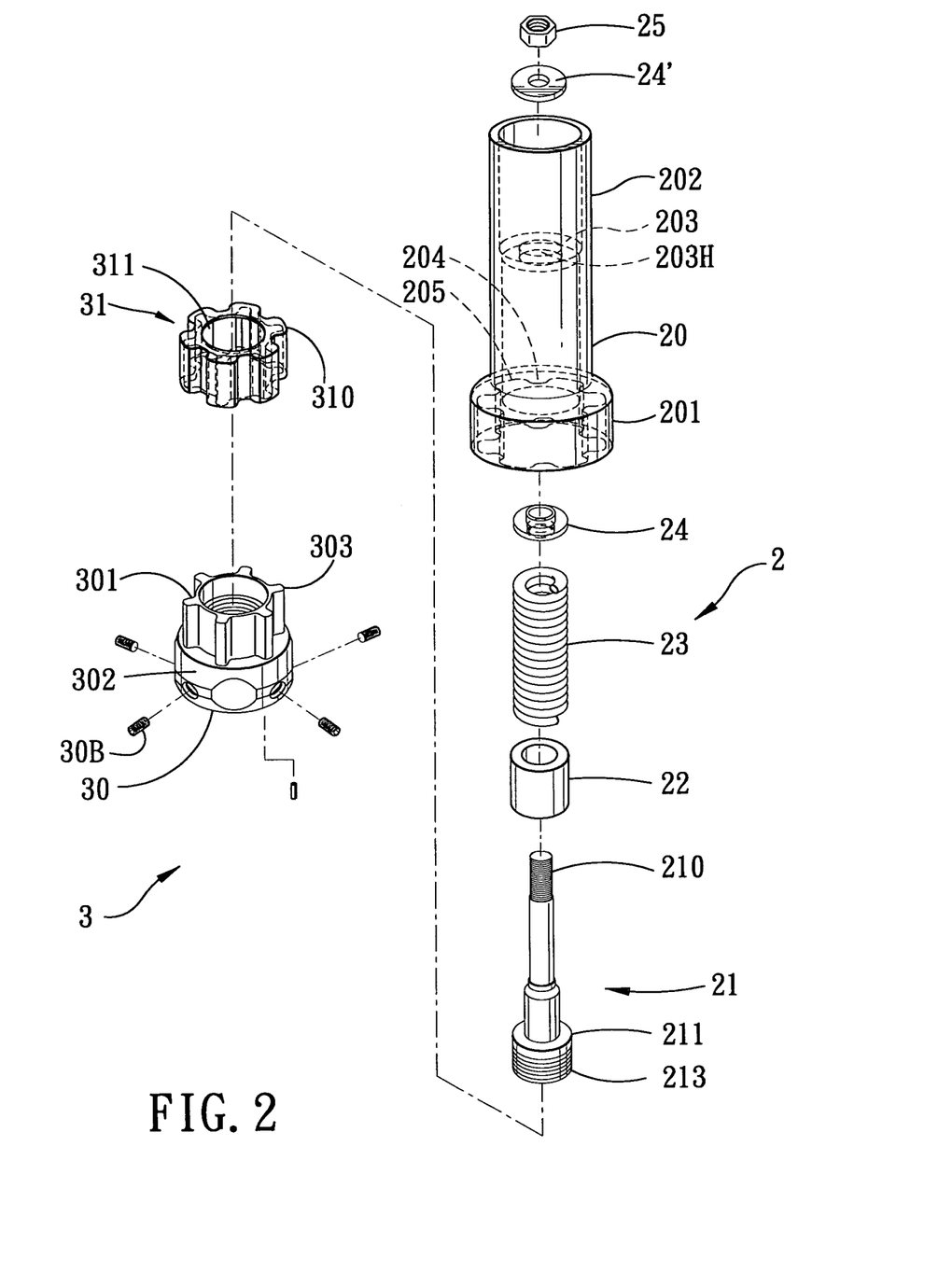
FIG. 2 is an exploded perspective view of the first preferred embodiment of a vibration-absorbing device for an artificial lower limb according to this invention.
Figure 3:
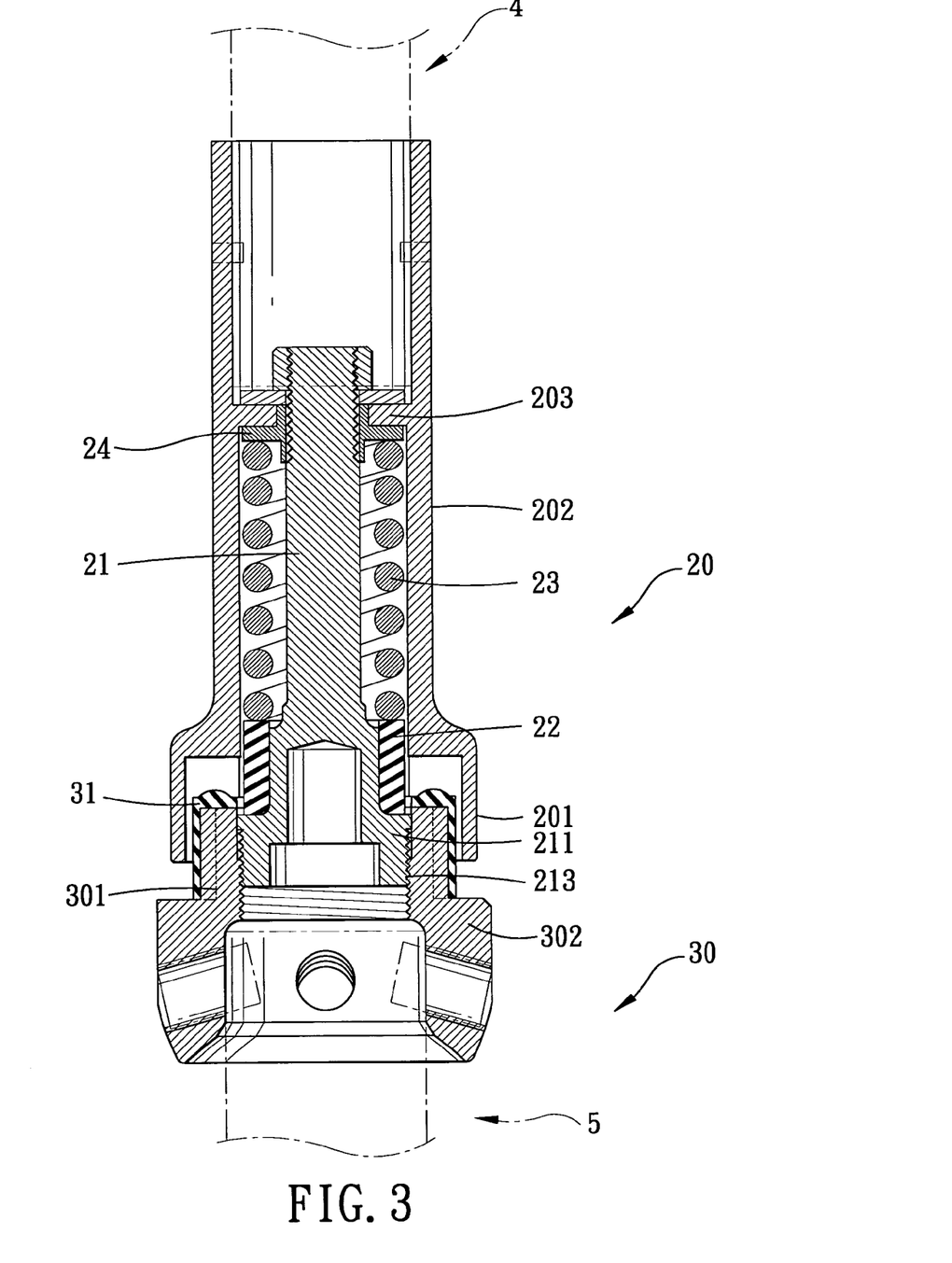
FIG. 3 is a sectional view of the first preferred embodiment.

Referring to FIGS. 2 and 3, the first preferred embodiment of a vibration-absorbing device for an artificial lower limb according to this invention is shown to include a longitudinal damping unit 2 and a transverse damping unit 3. The lower limb includes a prosthetic knee unit 4 and a prosthetic foot and ankle unit 5. The vibration-absorbing device is adapted to interconnect the prosthetic knee unit 4 and the prosthetic foot and ankle unit 5.

The longitudinal damping unit 2 includes an upright knee-connecting tube 20, a connecting rod 21, a lower stop unit including a sleeve 22, a coiled compression spring 23, a lower washer 24, and an upper stop unit consisting of an upper washer 24' and a nut 25.

The tube 20 has an open lower end with a cushion-receiving tube portion 201, an upper end adapted to be attached to the prosthetic knee unit 4, and an upper tube portion 202 that is formed integrally with an upper end of the cushion-receiving tube portion 201 at a lower end thereof. The upper tube portion 202 has an outer diameter that is smaller than inner and outer diameters of the cushion-receiving tube portion 201, and an inner surface that is formed with an inward flange 203 extending radially and inwardly therefrom and defining a central hole (203H). The cushion-receiving tube portion 201 has an inner surface that is formed with a plurality of spaced-apart axially extending ribs 204. Each adjacent pair of the ribs 204 defines an axial groove 205 therebetween. The axial grooves 205 have open lower ends.

The connecting rod 21 extends through the central hole (203H) in the inward flange 203 of the tube 20, and has an externally threaded upper end 210 engaging the nut 25, and a lower end flange 211 extending radially and outwardly therefrom.

The sleeve 22 is disposed around the connecting rod 21, and has an annular surface abutting against an upper end of the lower end flange 211 of the connecting rod 21.

The upper washer 24' is sleeved on the connecting rod 21 between the nut 25 and the inward flange 203 of the tube 20, and has an annular surface abutting against a top surface of the inward flange 203 of the tube 20. The upper washer 24' is sized so that it cannot pass through the central hole (203H) in the inward flange 203 of the tube 20 when the nut 25 is secured tightly to the connecting rod 21. Therefore, downward removal of the connecting rod 21 from the inward flange 203 of the tube 20 is prevented.

The lower washer 24 is sleeved on the connecting rod 21, and has an annular surface abutting against a bottom surface of the inward flange 203 of the tube 20.

Figure 4:
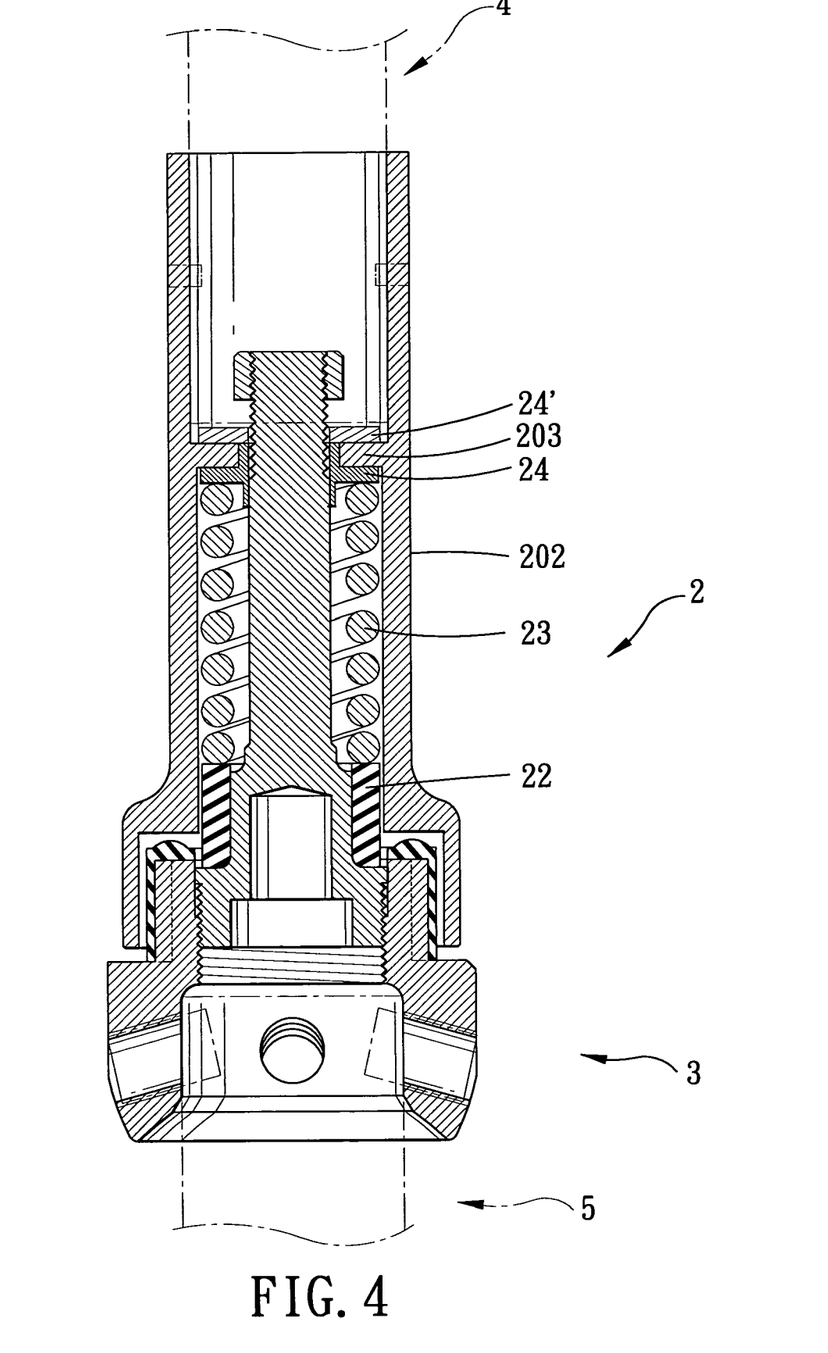
FIG. 4 is a sectional view of the first preferred embodiment, illustrating how axial movement of a knee-connecting tube relative to a connecting rod is retarded by a coiled compression spring.

The coiled compression spring 23 is sleeved on the connecting rod 21, and has an upper end abutting against the lower washer 24', and a lower end abutting against the sleeve 21 so as to bias the connecting rod 21 to move downwardly within the tube 20 to a predetermined position shown in FIG. 3. As s result, movement of the tube 20 relative to the connecting rod 21 is retarded when the tube 20 moves relative to the connecting rod 21 in an axial direction of the tube 20, as shown in FIG. 4.

The transverse damping unit 3 includes an ankle-connecting member 30 and a tubular cushion member 31 that is made of a resilient material.

The ankle-connecting member 30 has an internally threaded upper portion 301 engaging an externally threaded lower end 213 of the connecting rod 21, and a lower portion 302 attached to the foot and ankle unit 5 by a plurality of lock bolts (30B). The upper portion 301 has an annular outer surface that is formed with a plurality of spaced-apart axially extending ribs 303.

Figure 5:
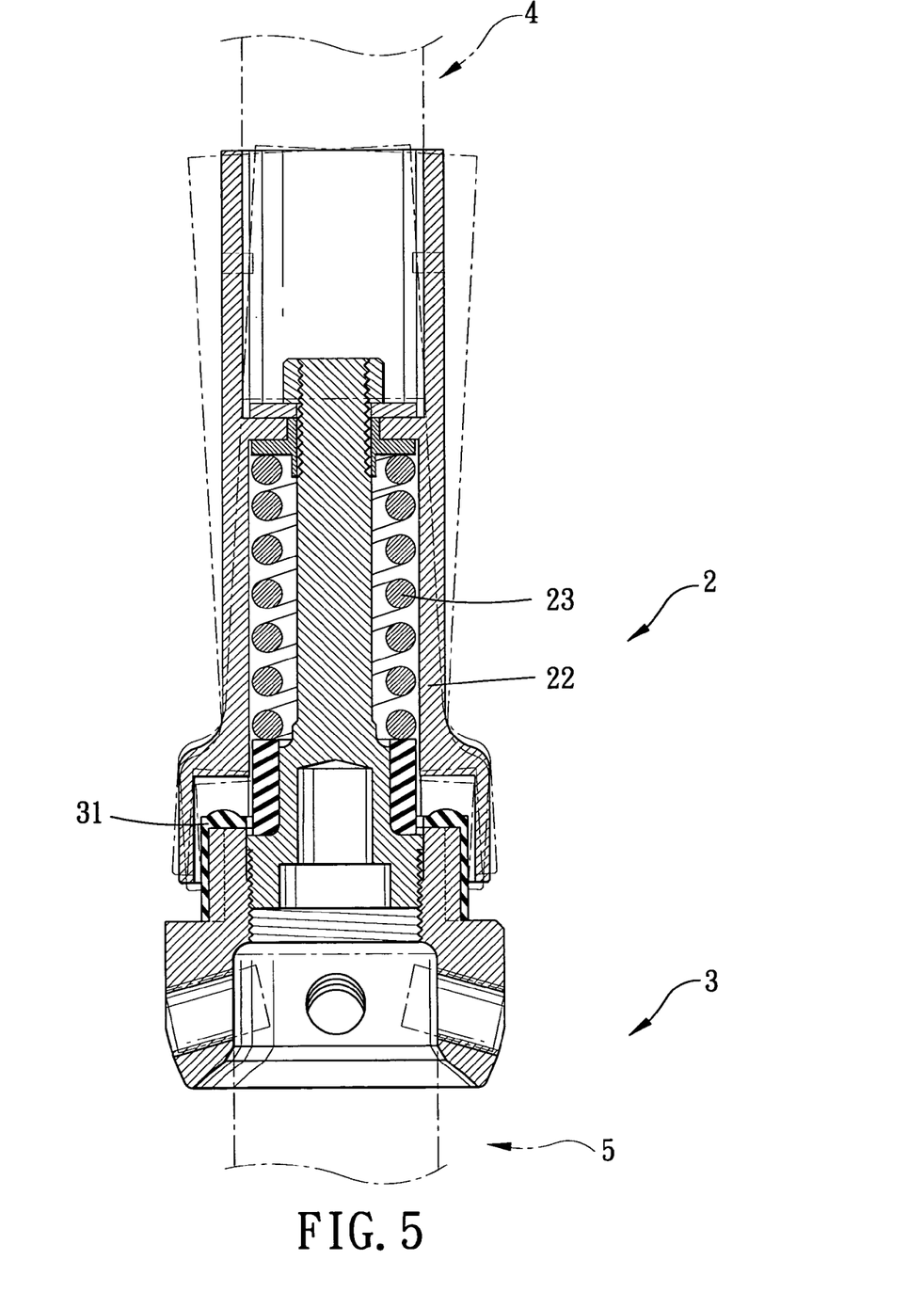
FIG. 5 is a sectional view of the first preferred embodiment, illustrating how transverse movement of the tube relative to the connecting rod is retarded.

The cushion member 31 is sleeved on the upper portion 301 of the ankle-connecting member 30, is disposed within the cushion-receiving tube portion 201 of the tube 20, and is formed with a plurality of hollow axially extending ribs 310 that define a plurality of slots 311 in an inner surface of the cushion member 31. The ribs 303 of the ankle-connecting member 30 engage respectively and fittingly the slots 311 in the cushion member 31, and are received respectively and slidably within the axial grooves 205 in the cushion-receiving tube portion 201 of the tube 20. Because inner and outer surfaces of the cushion member 31 are adjacent respectively to the outer surface of the upper portion 301 of the ankle-connecting member 30 and the inner surface of the cushion-receiving tube portion 201 of the tube 20, when the tube 20 moves relative to the connecting rod 21 in a transverse direction of the tube 20, as shown in FIG. 5, movement of the tube 20 relative to the connecting rod 21 can be retarded.

Figure 6:
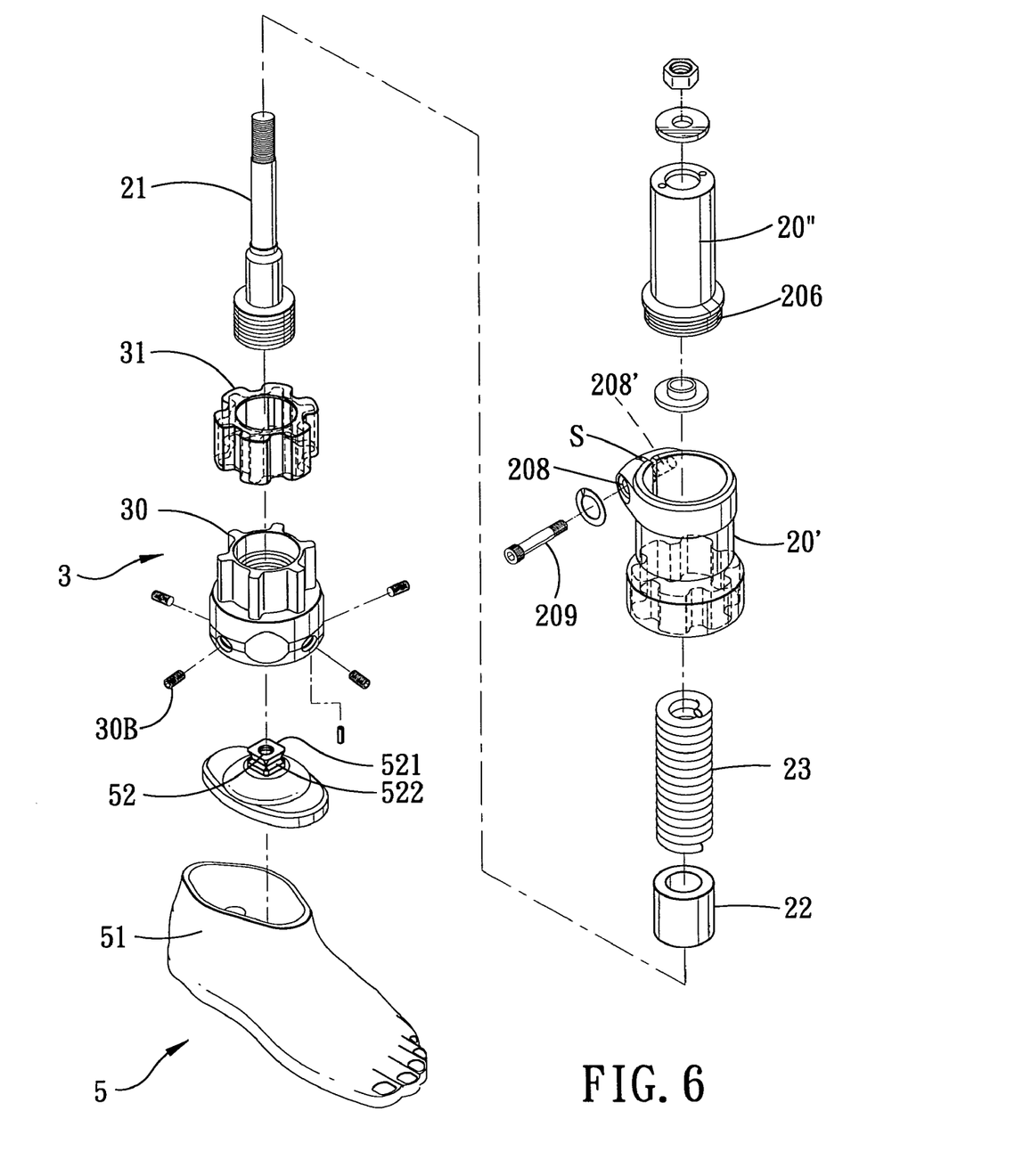
FIG. 6 is an exploded perspective view of the second preferred embodiment of a vibration-absorbing device for an artificial lower limb according to this invention.
Figure 7:
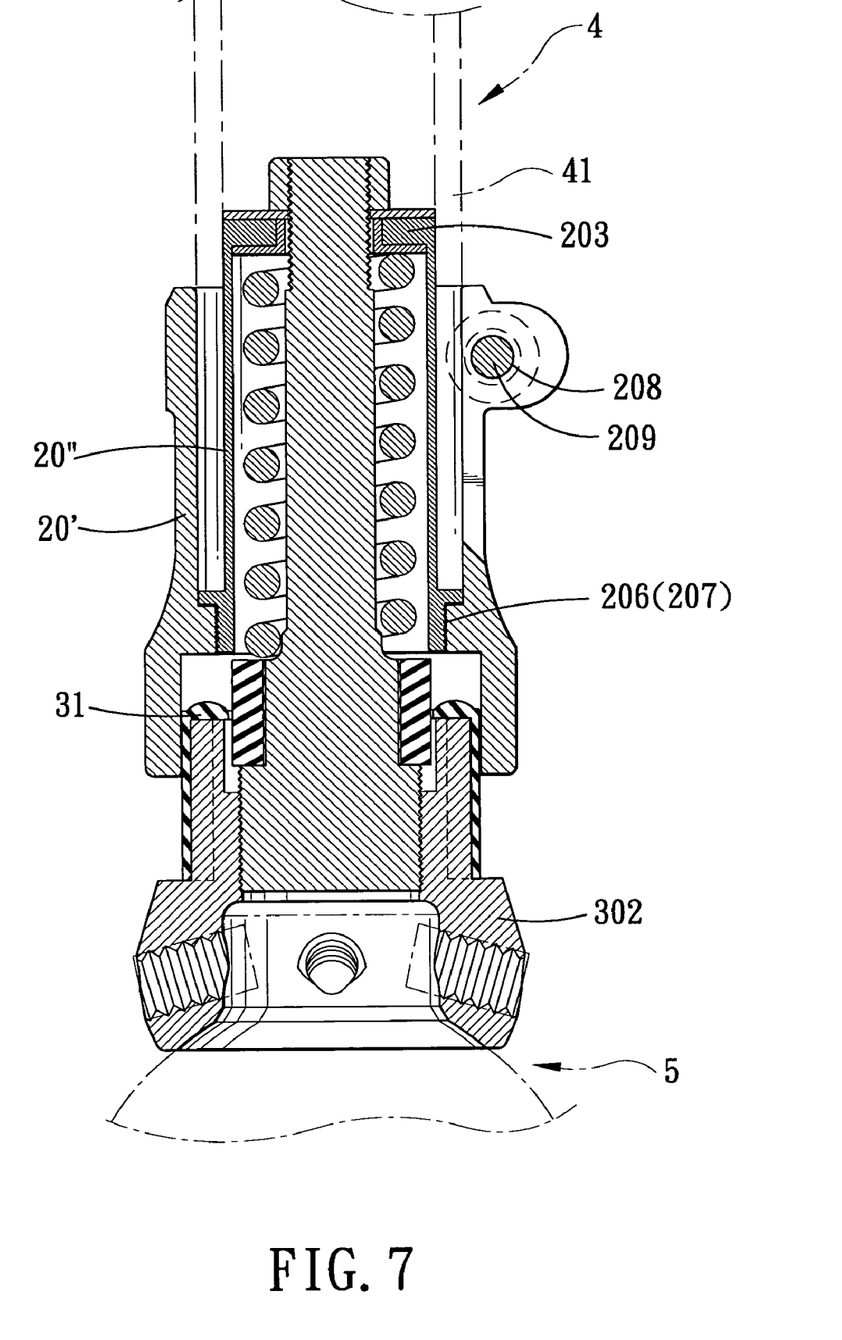
FIG. 7 is a sectional view of the second preferred embodiment.

FIGS. 6 and 7 show a modified knee-connecting tube, which includes an outer tube 20' and an inner tube 20" that has an externally threaded lower end 206 engaging an internally threaded portion 207 of the outer tube 20'. The inward flange 203 is formed at an upper end of the inner tube 20". The prosthetic knee unit 4 has a tubular connecting portion 41 that is inserted into a space between the inner and outer tubes 20", 20'. An upper end of the outer tube 20' is formed with a vertical slot (S) that has an open upper end, a non-threaded hole 208, and a threaded hole 208'. The slot (S) is disposed between and is adjacent to the non-threaded hole 208 and the threaded hole 208'. A headed lock bolt 209 extends through the non-threaded hole 208, and engages the threaded hole 208' so as to clamp the tubular connecting portion 41 of the prosthetic knee unit 4 between the inner and outer tubes 20", 20', thereby attaching the inner and outer tubes 20", 20' to the prosthetic knee unit 4. The prosthetic foot and ankle unit 5 includes a foot member 51, and an ankle member 52 connected fixedly to the ankle member 51. The ankle member 52 is formed with an integral insert portion 521 that is inserted into the lower portion 302 of the ankle-connecting member 30 and that has an outer surface which is formed with an annular groove 522. The lock bolts (30B) press against the insert portion 521, and engage the annular groove 522 in the insert portion 521 so as to attach the ankle-connecting member 30 to the foot and ankle unit 5.

With this invention thus explained, it is apparent that numerous modifications and variations can be made without departing from the scope and spirit of this invention. It is therefore intended that this invention be limited only as indicated by the appended claims.

I claim:

1. A vibration-absorbing device for an artificial lower limb, the lower limb including a prosthetic knee unit and a prosthetic foot and ankle unit, said vibration-absorbing device being adapted to interconnect the prosthetic knee unit and the prosthetic foot and ankle unit and comprising:

a longitudinal damping unit including
an upright knee-connecting tube having an open lower end with a cushion-receiving tube portion, an upper end adapted to be attached to the prosthetic knee unit, and an inward flange that extends radially and inwardly from said tube and that defines a central hole,
an upright connecting rod extending through said central hole in said inward flange of said tube,
an upper stop unit attached to an upper end portion of said connecting rod and prevented from passing downwardly through said central hole in said inward flange of said tube so as to prevent downward removal of said connecting rod from said inward flange,
a lower stop unit attached to a lower end portion of said connecting rod, and
a coiled compression spring sleeved on said connecting rod between said lower stop unit and said inward flange of said tube so as to bias said connecting rod to move downwardly within said tube, thereby retarding movement of said tube relative to said connecting rod in an axial direction of said tube; and
a transverse damping unit including
an ankle-connecting member adapted to be attached to the prosthetic foot and ankle unit and connected fixedly to a lower end of said connecting rod, and
a tubular cushion member sleeved on an upper portion of said ankle-connecting member and disposed within said cushion-receiving tube portion of said tube, said cushion member being made of a resilient material and having an inner surface disposed adjacent to an outer surface of said ankle-connecting member, and an outer surface disposed adjacent to an inner surface of said cushion-receiving tube portion of said tube so as to retard movement of said tube relative to said ankle-connecting member in a transverse direction of said tube.

2. The vibration-absorbing device as claimed in claim 1, wherein said connecting rod has an externally threaded lower end, said cushion-receiving tube portion of said tube having an inner surface that is formed with a plurality of axial grooves which has an open lower end, said ankle-connecting member having an internally threaded upper portion that engages said lower end of said connecting rod and that has an annular outer surface which is formed with a plurality of spaced-apart axially extending ribs, said cushion member being formed with a plurality of hollow axially extending ribs that define a plurality of slots in an inner surface of said cushion member and that are received respectively and slidably within said axial grooves in said cushion-receiving tube portion of said tube, said slots in said cushion members engaging respectively and fittingly said ribs of said ankle-connecting member.

3. The vibration-absorbing device as claimed in claim 1, wherein said tube further has an upper tube portion that is formed integrally with an upper end of said cushion-receiving tube portion at a lower end thereof and that has an outer diameter which is smaller than inner and outer diameters of said cushion-receiving tube portion, said inward flange being formed in an inner surface of said upper tube portion of said tube;

wherein said connecting rod has a lower end flange extending radially and outwardly therefrom;

wherein said lower stop unit includes a sleeve that is disposed around said connecting rod and that has a lower end surface which abuts against an upper end of said lower end flange of said connecting rod; and wherein said coiled compression spring has a lower end abutting against an upper end of said sleeve.

4. The vibration-absorbing device as claimed in claim 1, wherein said connecting rod has an externally threaded upper end, said upper stop unit including a nut engaging said externally threaded upper end of said connecting rod, and an upper washer that is sleeved on said connecting rod between said nut and said inward flange of said tube and that has an annular surface abutting against a top surface of said inward flange of said tube.

* * * * *